(12) United States Patent
Vyakarnam et al.

(10) Patent No.: US 6,355,699 B1
(45) Date of Patent: Mar. 12, 2002

(54) PROCESS FOR MANUFACTURING BIOMEDICAL FOAMS

(75) Inventors: Murty N. Vyakarnam, Edison; Mark B. Roller, North Brunswick; David V. Gorky, Flemington; Angelo George Scopelianos, Whitehouse Station, all of NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/345,095

(22) Filed: Jun. 30, 1999

(51) Int. Cl.$^7$ .............................. C08J 9/26; C08F 6/00; C08K 11/00
(52) U.S. Cl. .................. 521/61; 525/437; 525/444; 524/9; 524/21; 524/56; 524/58; 524/81; 524/401; 524/425; 524/433; 424/443; 424/486; 521/62; 521/64; 521/82; 521/84.1; 521/102; 521/134; 521/138; 528/488; 528/491
(58) Field of Search ..................... 525/437, 444; 524/81, 9, 21, 56, 58, 401, 433, 425; 424/443, 486; 521/61, 62, 64, 82, 84.1, 50, 102, 134, 138; 528/488, 491

(56) References Cited

U.S. PATENT DOCUMENTS

| | | | | |
|---|---|---|---|---|
| 4,186,448 A | * | 2/1980 | Brekke | 623/16 |
| 5,102,983 A | * | 4/1992 | Kennedy | 528/354 |
| 5,133,755 A | * | 7/1992 | Brekke | 623/16 |
| 5,263,629 A | * | 11/1993 | Trumbull et al. | 227/181.1 |
| 5,468,253 A | * | 11/1995 | Bezwada et al. | 606/230 |
| 5,514,378 A | * | 5/1996 | Mikos et al. | 424/425 |
| 5,522,895 A | * | 6/1996 | Mikos | 623/16 |
| 5,607,474 A | * | 3/1997 | Athanasiou et al. | 623/11 |
| 5,677,355 A | * | 10/1997 | Shalaby et al. | 521/61 |
| 5,686,091 A | * | 11/1997 | Leong et al. | 424/426 |
| 5,716,413 A | * | 2/1998 | Walter et al. | 623/16 |
| 5,752,965 A | * | 5/1998 | Francis et al. | 606/151 |
| 5,755,792 A | * | 5/1998 | Brekke | 623/16 |
| 5,769,899 A | * | 6/1998 | Schwartz et al. | 623/18 |
| 5,770,193 A | * | 6/1998 | Vacanti et al. | 424/93.7 |

FOREIGN PATENT DOCUMENTS

WO    WO 99/09149    2/1999

* cited by examiner

*Primary Examiner*—Samuel A. Acquah

(57) ABSTRACT

The present invention provides an improved lyophilization process for forming biocompatible foam structures. The process allows the foam structures to be tailored for specific end uses. The foams formed by this process are well suited to be used in medical applications such as tissue engineering. The foam structures may also contain pharmaceutically active substances

36 Claims, 10 Drawing Sheets

100 μm

100 μm

100 μm

100 μm 1 mm 1 mm 1 mm 1 mm 1 mm

100 μm

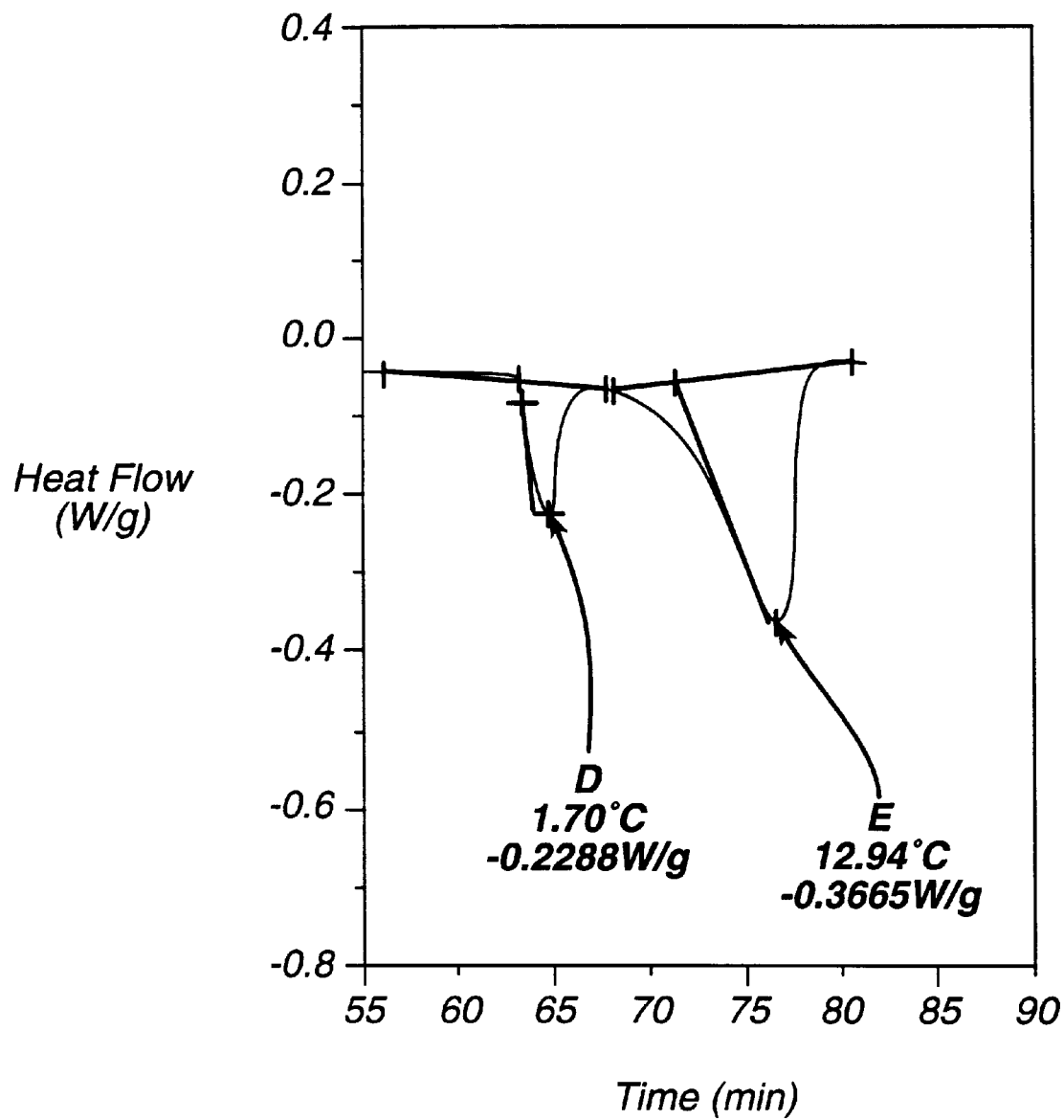

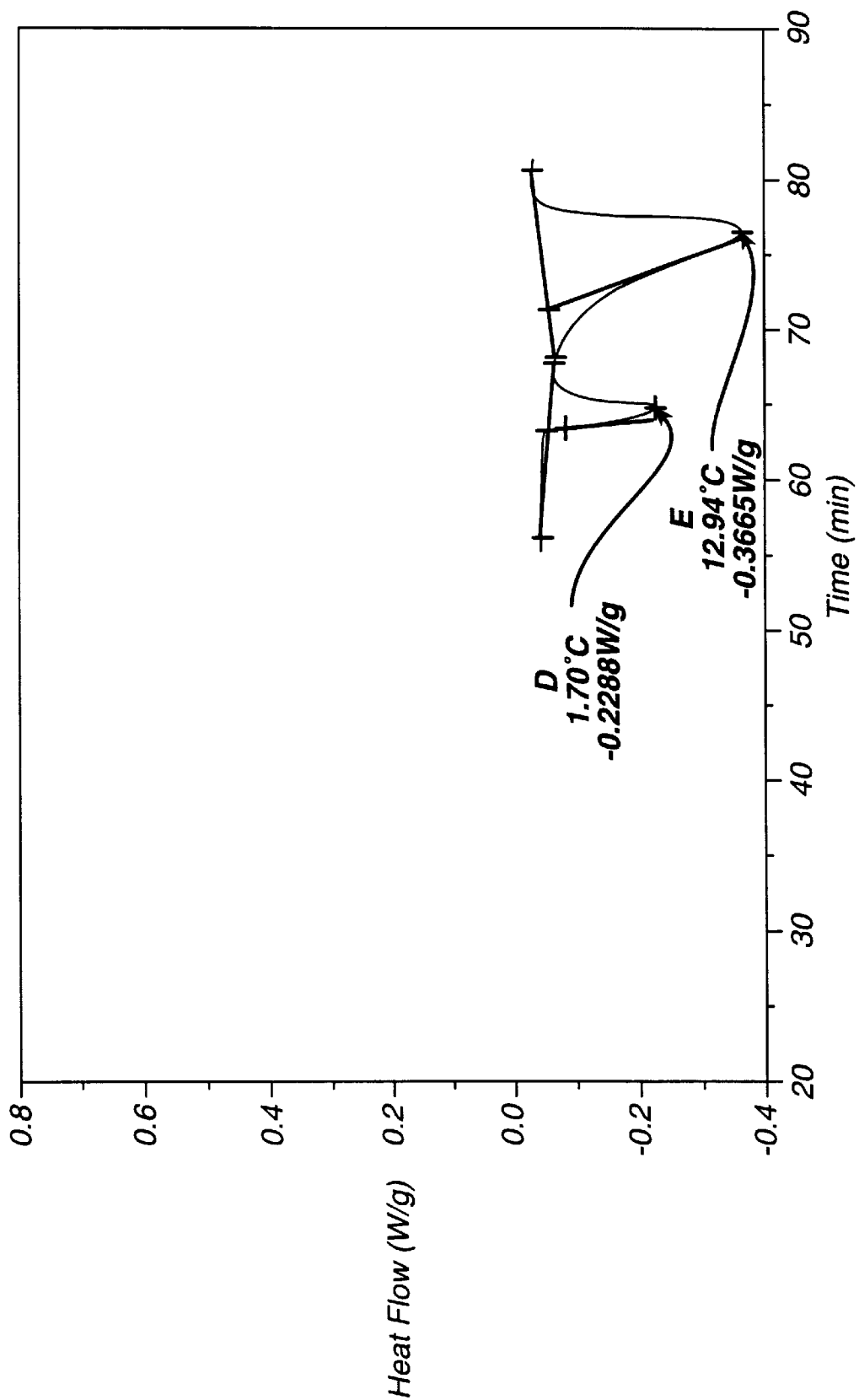

PROCESS FOR MANUFACTURING BIOMEDICAL FOAMS

FIELD OF THE INVENTION

This invention relates to the field of porous foams and methods of preparing these materials. In particular it relates to the art of making porous foams (that are preferably continuous and open celled) from absorbable polymers for biomedical applications using lyophilization.

BACKGROUND OF THE INVENTION

There is a growing demand for foams for biomedical applications such as buttress materials (U.S. Pat. No. 5,752,965; U.S. Pat. No. 5,263,629; EPA 594 148 A1); scaffolds for tissue engineering (U.S. Pat. No. 5,607,474; WO 94/25079); wound healing dressing; 3D devices such as porous grafts; and other implantable wound healing, augmentation, and regeneration devices (U.S. Pat. No. 5,677,355) etc. Specifically these foams have been made from biocompatible polymers and have had a uniform and open celled microstructure.

Open cell porous biocompatible foams have been recognized to have significant potential for use in the repair and regeneration of tissue. Early efforts in tissue repair focused on the use of biocompatible foam as porous plugs to fill voids in bone. Brekke, et al. (U.S. Pat. No. 4,186,448) described the use of porous mesh work of plugs composed of polyhydroxy acid polymers such as polylactide for healing bone voids. Several attempts have been made in the recent past to make tissue engineering scaffolds using different methods, for example U.S. Pat. No. 5,522,895 (Mikos) and U.S. Pat. No. 5,514,378 (Mikos, et al) using leachables; U.S. Pat. No. 5,755,792 (Brekke) and U.S. Pat. No. 5,133,755 (Brekke) using vacuum foaming techniques; U.S. Pat. No. 5,716,413 (Walter, et al) and U.S. Pat. No. 5,607,474 (Athanasiou, et al) using precipitated polymer gel masses; U.S. Pat. No. 5,686,091 (Leong, et al) and U.S. Pat. No. 5,677,355 (Shalaby, et al) using polymer melt with a fugitive compound that sublimes at temperatures greater than room temperature; and U.S. Pat. No. 5,770,193 (Vacanti, et al) and U.S. Pat. No. 5,769,899 (Schwartz, et al) using textile-based fibrous scaffolds. Hinsch et al (EPA 274,898) described a porous open cell foam of polyhydroxy acids with pore sizes from about 10 to about 200 microns for the in-growth of blood vessels and cells. The foam described by Hincsh could also be reinforced with fibers, yarns braids, knitted fabrics, scrims and the like. Hincsh's work also described the use of a variety of polyhydroxy acid polymers and copolymers such as poly-L-lactide, poly-DL-lactide, polyglycolide, and polydioxanone. The Hincsh foams had the advantage of having regular pore sizes and shapes that could be controlled by the processing conditions, solvent selected and additives.

Lyophilization lends itself to many advantages when processing thermally sensitive polymers. Further, it lends itself to aseptic processing methodologies for biomedical applications especially when using combinations of polymers with drugs or other bio-active agents such as growth factors, proteins etc. The chief drawback of this process in prior art is that it is the most time consuming and expensive step in the manufacturing operations. It has been realized for some time now that reducing the cycle time will provide significant cost benefits and make this process an even more attractive manufacturing method especially for absorbable polymers, proteins and combinations of these materials incorporating drugs, fillers, excipients, etc. There have been some instances, where this process has been used to make foams from absorbable polymers, but the process of lyophilization in making these foams is far from optimum (U.S. Pat. No. 5,468,253; EPA 274 898 A2; EPA 594 148 A1); often taking more than 3 days to process one batch.

It is therefore, an object of this invention to provide a faster and more economical lyophilization process to make foams for medical foams.

It is a further object of the present invention to provide a lyophilization process for providing foams that are particularly well suited for tissue engineering.

SUMMARY OF THE INVENTION

We have discovered a process for making biomedical absorbable foams comprising solidifying a solution of a solvent and a bioabsorbable polymer to form a solid then at a temperature above the apparent Tg of the solid, but below the freezing temperature of the solution, then subliming the solvent out of the solid to provide a biocompatible porous foam.

We have also discovered a process for making biomedical foams with channels therein, comprising solidifying a mixture of a solvent and a bioabsorbable polymer to form a substantially solidified but not completely solidified material, then subliming the solvent out of the material to provide a biocompatible porous foam that has channels.

We have also discovered a process for making biomedical foams with a gradient of pore size therein comprising solidifying a mixture of a solvent and a bioabsorbable polymer to form a substantially solidified but not completely solidified material, then subliming the solvent out of the material to provide a biocompatible porous foam that has a gradient of pores.

These and other objects and advantages of the present invention will be apparent to those skilled in the art from the following Figures, Detailed Description, and Examples.

BRIEF DESCRIPTION OF THE FIGURES

FIGS. 6A and 6B are DSC of a 10 percent weight by weight solution of a 35/65 mole percent ε-caprolactoneco-glycolide in 1,4-dioxane. In FIG. 6A C indicates the apparent glass transition at about −21° C. In FIG. 6B points D and E on the DSC indicates the meltdowns of the frozen solid (on heating). To observe these thermal events the heating rates should be approximately 1 degree a minute.

FIG. 7 is a perspective view of a mold that could be used to make shaped foamed parts.

DETAILED DESCRIPTION OF THE INVENTION

Figure 1A:
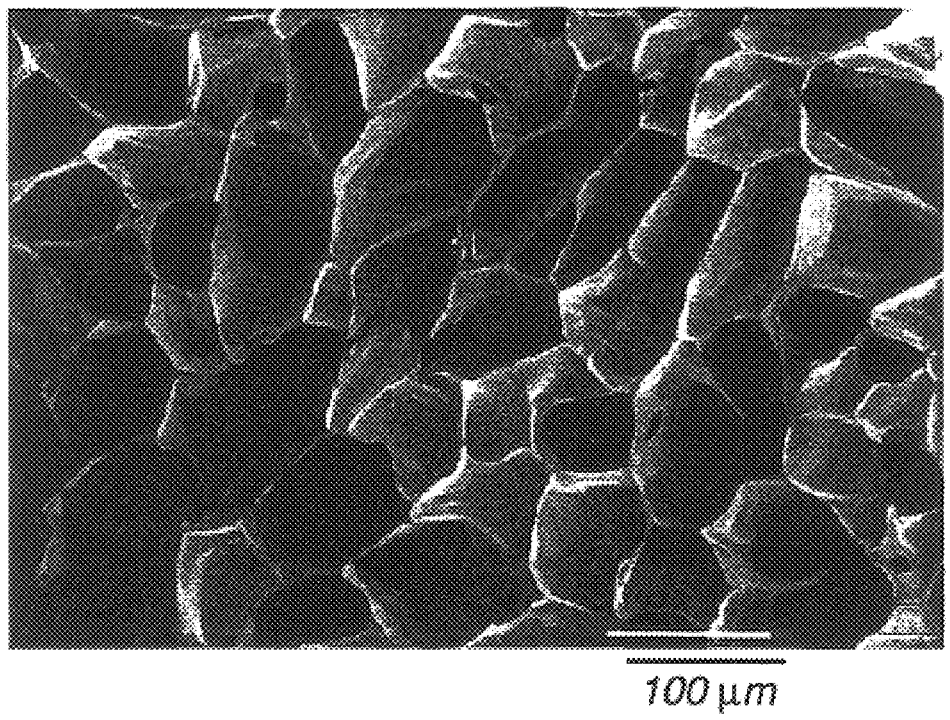
FIGS. 1A and 1B are scanning electron micrographs comparing foams made by a slow cooling 1A (right) versus fast cooling 1B (left).
Figure 1B:
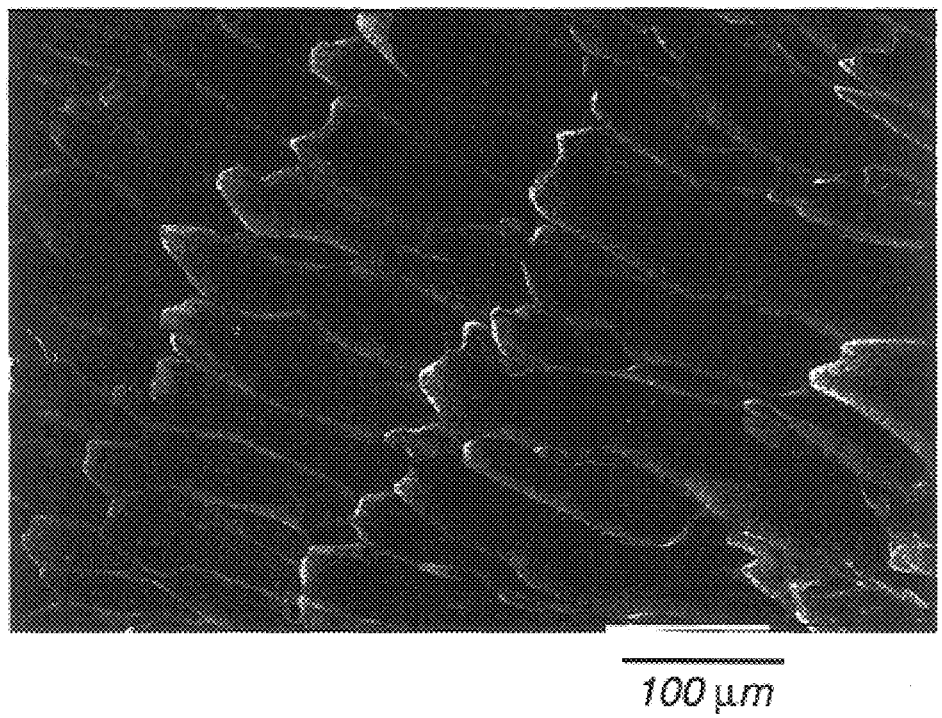

Sublimation (primary drying) is the most critical step in reducing the overall cycle time in the lyophilization process. An efficient sublimation process helps in increasing the temperature at which the secondary drying can take place. Contrary to conventional teachings, we have discovered that sublimation of polymer-solvent system can be conducted above the apparent glass transition of the polymer-solvent system. In theory, but in no way limiting the scope of this invention, it is believed that the frozen microstructure of the polymer-solvent system has enough structural integrity even at temperatures greater than the glass transition to permit sublimation to occur without the foam collapsing. Unlike typical aqueous systems with low molecular weights, the long chains and/or crystalline regions in a polymer may be providing dimensional stability to the frozen microstructure even at temperatures greater than the apparent glass transition of the mixture. Therefore, the solvent sublimation during the primary drying step can be maximized by operating at a temperature above the apparent glass transition temperature and about the solidification temperature of the mixture (preferably just below). The cascading effect of operating at higher temperatures during the primary step (and optionally secondary drying step) results in reducing the overall cycle time and the residual solvent in the foams at the end of the lyophilization cycle.

This invention also provides methods for making porous bioabsorbable polymer foams with a variety of architectures. The features of such foams can be controlled to suit desired application by a modified lyophilization process that results in one or more of the following: (1) interconnecting pores of sizes ranging from 10 to 200 microns (or greater) that provide pathways for cellular ingrowth and nutrient diffusion; (2) a variety of porosities preferably ranging from 80% to greater than 95%; (3) gradient in the pore size across one direction for preferential cell culturing; (4) channels that run through thickness of the foam for improved vascularization and nutrient diffusion; (5) micro-patterning of pores on surface for cellular organization; (6) tailorability of pore shape: spherical, ellipsoidal, columnar to suit cell shape and size; (7) anisotropic mechanical properties; (8) composite foams with polymer composition gradient to elicit different cell response on each surface to create functional tissue; (9) blends of different polymer compositions to create structures that have portions that will break down at different rates; (10) colyophilized or coated with pharmaceutically active compounds including but not limited to biological factors such as (peptides including RGD's, growth factors and the like); (11) ability to make three dimensional shapes and devices with preferred microstructures; and (12) colyophilization with other parts or medical devices to provide a porous surface coating or composite structure. These controlled features in absorbable polymers have distinct advantages over the prior art where the scaffolds are typically isotropic in mechanical properties or have random microstructures with no preferred morphology at the pore level. However, it is preferred that foams used in tissue scaffolds have a structure that provides organization at the microstructural level that provides a template that facilitates cellular organization that mimic natural tissue. The cells will adhere, proliferate and differentiate along the contours of the structure. This will ultimately result in a cultured tissue that mimics the anatomical features of real tissues to a large extent.

The foams that are made in this invention are made by polymer-solvent phase separation technique with modifications to the prior art. Generally, a polymer solution can be separated into two phases by any one of the four techniques: (a) thermally induced gelation/crystalization; (b) nonsolvent induced separation of solvent and polymer phases; (c) chemically induced phase separation, and (d) thermally induced spinodal decomposition. The polymer solution is separated in a controlled manner into either two distinct phases or two bicontinuous phases. Subsequent removal of the solvent phase usually leaves a porous structure of density less than the bulk polymer and pores in the micrometer ranges (ref. "Microcellular foams via phase separation" by A. T. Young, J. Vac. Sci. Technolol. A 4(3), May/June 1986). The steps involved in the preparation of these foams consists of choosing the right solvents for the polymers that will be lyophilized and preparing a homogeneous solution. Next, the polymer solution is subjected first to a freezing cycle then to a vacuum drying cycle. The freezing step phase separates the polymer solution by one of the above four techniques and vacuum drying step removes the solvent by sublimation and/or drying leaving a porous polymer structure or a inter-connected open cell porous foam.

Examples of suitable biocompatible, bioabsorbable polymers that could be used include polymers selected from the group consisting of aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amine groups, poly(anhydrides), polyphosphazenes, biomolecules and blends thereof. For the purpose of this invention aliphatic polyesters include but are not limited to homopolymers and copolymers of lactide (which includes lactic acid, d-, l- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\delta$-valerolactone, $\beta$-butyrolactone, $\gamma$-butyrolactone, $\epsilon$-decalactone, hydroxybutyrate (repeating units), hydroxyvalerate (repeating units), 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly(iminocarbonate) for the purpose of this invention include as described by Kemnitzer and Kohn, in the *Handbook of Biodegradable Polymers*, edited by Domb, Kost and Wisemen, Hardwood Academic Press, 1997, pages 251–272. Copoly(ether-esters) for the purpose of this invention include those copolyester-ethers described in "Journal of Biomaterials Research", Vol. 22, pages 993–1009, 1988 by Cohn and Younes and Cohn, Polymer Preprints (ACS Division of Polymer Chemistry) Vol. 30(1), page 498, 1989 (e.g. PEO/PLA). Polyalkylene oxalates for the purpose of this invention include U.S. Pat. Nos. 4,208,511; 4,141,087; 4,130,639; 4,140,678; 4,105,034; and 4,205,399 (incorporated by reference herein). Polyphosphazenes, co-, ter- and higher order mixed monomer based polymers made from L-lactide, D,L-lactide, lactic acid, glycolide, glycolic acid, para-dioxanone, trimethylene carbonate and $\epsilon$-caprolactone such as are described by Allcock in *The Encyclopedia of Polymer Science*, Vol. 13, pages 31–41, Wiley Intersciences, John Wiley & Sons, 1988 and by Vandorpe, Schacht, Dejardin and Lemmouchi in the *Handbook of Biodegradable Polymers*, edited by Domb, Kost and Wisemen, Hardwood Academic Press, 1997, pages 161–182 (which are hereby incorporated by reference herein). Polyanhydrides from diacids of the form HOOC—$C_6H_4$—O—$(CH_2)_m$—O—$C_6H_4$—COOH where m is an integer in the range of from 2 to 8 and copolymers thereof with aliphatic alpha-omega diacids of up to 12 carbons. Polyoxaesters polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150 (which are incorporated herein by reference). Polyorthoesters such as those described by Heller in *Handbook of Biodegradable Polymers*, edited by Domb, Kost and Wisemen, Hardwood Academic Press, 1997, pages 99–118 (hereby incorporated herein by reference).

Particularly well suited polymers for the purpose of this invention are aliphatic polyesters which include but are not limited to homopolymers and copolymers of lactide (which includes lactic acid D-,L- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate (repeating units), hydroxyvalerate (repeating units), 1,4-dioxepan-2-one (including its dimer 1,5,8,12-tetraoxacyclotetradecane-7,14-dione), 1,5-dioxepan-2-one, 6,6-dimethyl-1,4-dioxan-2-one and polymer blends thereof. One preferred class of polymers are elastomeric copolymers. For the purpose of this invention an "elastomeric copolymers" are defined as a materials that at room temperature can be stretched repeatedly to at least about twice its original length and upon immediate release of stress, will return to approximately its original length. Suitable bioabsorbable, biocompatible elastomers include but are not limited to those selected from the group consisting of elastomeric copolymers of ε-caprolactone and glycolide (preferably having a mole ratio of ε-caprolactone to glycolide of from about 30:70 to about 70:30, preferably 35:65 to about 65:35, and more preferably 45:55 to 35:65); elastomeric copolymers of ε-caprolactone and lactide, including L-lactide, D-lactide blends thereof or lactic acid copolymers (preferably having a mole ratio of ε-caprolactone to lactide of from about 35:65 to about 65:35 and more preferably 45:55 to 30:70;) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40); elastomeric copolymers of ε-caprolactone and p-dioxanone (preferably having a mole ratio of ε-caprolactone to p-dioxanone of from about 30:70 to about 70:30); elastomeric copolymers of p-dioxanone and trimethylene carbonate (preferably having a mole ratio of p-dioxanone to trimethylene carbonate of from about 30:70 to about 70:30); elastomeric copolymers of trimethylene carbonate and glycolide (preferably having a mole ratio of trimethylene carbonate to glycolide of from about 30:70 to about 70:30); elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. Examples of suitable bioabsorbable elastomers are described in U.S. Pat. Nos. 4,045,418; 4,057,537 and 5,468,253 all hereby incorporated by reference. These elastomeric polymers will have an inherent viscosity of from about 0.75 dL/g to about 4 dL/g, preferably an inherent viscosity of from about 1.2 dL/g to about 2 dL/g and most preferably an inherent viscosity of from about 1.4 dL/g to about 2 dL/g as determined at 25° C. in a 0.1 gram per deciliter (g/dL) solution of polymer in hexafluoroisopropanol (HFIP).

One preferred embodiment of the present invention is to use polymer blends to prepare foams. By using polymer blends a foam material may be formed that transitions from one composition to another composition in a gradient like architecture. Specific examples of techniques for making gradient foam devices are described in the Examples. Foams having this gradient architecture are particularly advantageous in tissue engineering applications to mimic the structure of naturally occurring tissue such as cartilage, skin, bone and vascular tissue. For example by blending an elastomer of ε-caprolactone-co-glycolide with ε-caprolactone-co-lactide (i.e. with a mole ratio of about 5:95) a foam may be formed that transitions from a softer spongy foam to a stiffer more rigid foam similar to the transition from cartilage to bone. Clearly other polymer blends may be used for similar gradient effects or to provide different gradients such as different absorption profiles, stress response profiles, or different degrees of elasticity.

To practice the present invention, first an appropriate absorbable polymer or polymers, which are to be foamed are selected. Having selected the polymer, the next procedure is the selection of the appropriate compatible solvent and the relative amounts of polymer and solvent to be utilized. Blends of one or more polymers also may be utilized in the practice of the present invention. Functionally, the polymer and solvent are mixed at an appropriate temperature to form a clear, homogeneous solution. If a solution cannot be formed at any solvent concentration, then the solvent is inappropriate and cannot be utilized with that particular polymer.

Where blends of one or more polymers are used, as should be understood, useful solvents must typically be operable with all of the polymers included. It may however be possible for the polymer blend to have characteristics such that the solvent need not be operable with all polymers used. As one example, where one or more polymeric constituents are present in such relatively small amounts that will not significantly affect the properties of the blend, the solvent employed need only be operable with the principal polymer or polymers.

Because absolute predictability for predetermining the suitability of a particular solvent with a particular polymer is not possible routine experimentation may be necessary. The normal guidelines for selecting a solvent for compounds applies to polymer systems. Thus when the polymer involved is non-polar, non-polar solvents with similar solubility parameters at the solution temperature are more likely to be useful. When such parameters are not available, one may refer to the more readily available room temperature solubility parameters, for general guidance. Similarly, with polar polymers, polar organic solvents with similar solubility parameters should be initially examined. Also, the relative polarity or non-polarity of the solvent should be matched with the relative polarity or non-polarity of the polymer. Preferred are solvents with low boiling points and high freezing temperatures that have high vapor pressures. With respect to appropriate solvents, particular species of various types of organic compounds have been found useful, including aliphatic and aromatic acids, aliphatic, aromatic and cyclic alcohols, aldehydes, amides, esters and diesters, ethers, ketones and various hydrocarbons and heterocycles.

Also, while most useful materials are liquid at ambient temperatures, materials which are solid at room temperature may be employed so long as solutions can be formed with the polymer at elevated temperatures and the material does not interfere with the formation of the microporous structure.

Suitable solvents that should be generally suited as a starting place for selecting a solvent for the preferred absorbable aliphatic polyesters include but are not limited to solvents selected from a group consisting of formic acid, ethyl formate, acetic acid, hexafluoroisopropanol (HFIP), cyclic ethers (i.e. THF, DMF, and PDO), acetone, acetates of C2 to C5 alcohol (such as ethyl acetate and t-butylacetate), glyme (i.e. monoglyme, ethyl glyme, diglyme, ethyl diglyme, triglyme, butyl diglyme and tetraglyme) methylethyl ketone, dipropyleneglycol methyl ether, lactones (such as γ-valerolactone, δ-valerolactone, βbutyrolactone, γ-butyrolactone) 1,4-dioxane, 1,3-dioxolane, 1,3-dioxolane-2-one (ethylene carbonate), dimethlycarbonate, benzene, toluene, benzyl alcohol, p-xylene, naphthalene, tetrahydrofuran, N-methyl pyrrolidone, dimethylformamide, chloroform, 1,2-dichloromethane, morpholine, dimethylsulfoxide, hexafluoroacetone sesquihydrate (HFAS), anisole and mixtures thereof. Among these solvents, the preferred solvent is 1,4-dioxane. A homogeneous solution of the polymer in the solvent is prepared using standard techniques.

Accordingly, as will be appreciated, the applicable polymer concentration or amount of solvent, which may be utilized, will vary with each system. Suitable phase diagram curves for several systems have already been developed. However, if an appropriate curve is not available, this can be readily developed by known techniques. For example, a suitable technique is set forth in Smolders, van Aartsen and Steenbergen, Kolloid-Z. u. Z. Polymere, 243, 14 (1971). As a general guideline the amount of polymer in the solution can vary from about 0.5% to about 90% and preferably will vary from about 0.5% to about 30% by weight depending to a large extent on the solubility of the polymer in a given solvent and the final properties of the foam desired.

Additionally, solids may be added to the polymer-solvent system. The solids added to the polymer-solvent system preferably will not react with the polymer or the solvent. Suitable solids include materials that promote tissue regeneration or regrowth, buffers, reinforcing materials or porosity modifiers. Suitable solids include, but are not limited to, particles of demineralized bone, calcium phosphate particles, or calcium carbonate particles for bone repair, leachable solids for pore creation and particles of bioabsorbable polymers not soluble in the solvent system as reinforcing or to create pores as they are absorbed. Suitable leachable solids include but are not limited nontoxic leachable materials selected from the group consisting of salts (i.e. sodium chloride, potassium chloride, calcium chloride, sodium tartrate, sodium citrate, and the like) biocompatible mono and disaccharides (i.e. glucose, fructose, dextrose, maltose, lactose and sucrose), polysaccharides (i.e. starch, alginate), water soluble proteins (i.e. gelatin and agarose). Generally all of these materials will have an average diameter of less than about 1mm and preferably will have an average diameter of from about 50 to about 500 microns. The particles will generally constitute from about 1 to about 50 volume percent of the total volume of the particle and polymer-solvent mixture (wherein the total volume percent equals 100 weight percent). The leachable materials can be removed by immersing the foam with the leachable material in a solvent in which the particle is soluble for a sufficient amount of time to allow leaching of substantially all of the particles, but which does not dissolve or detrimentally alter the foam. The preferred extraction solvent is water, most preferably distilled-deionized water. This process is described in U.S. Pat. No. 5,514,378 hereby incorporated herein by reference (see column 6). Preferably the foam will be dried after the leaching process is complete at low temperature and/or vacuum to minimize hydrolysis of the foam unless accelerated absorption of the foam is desired.

Figure 5:
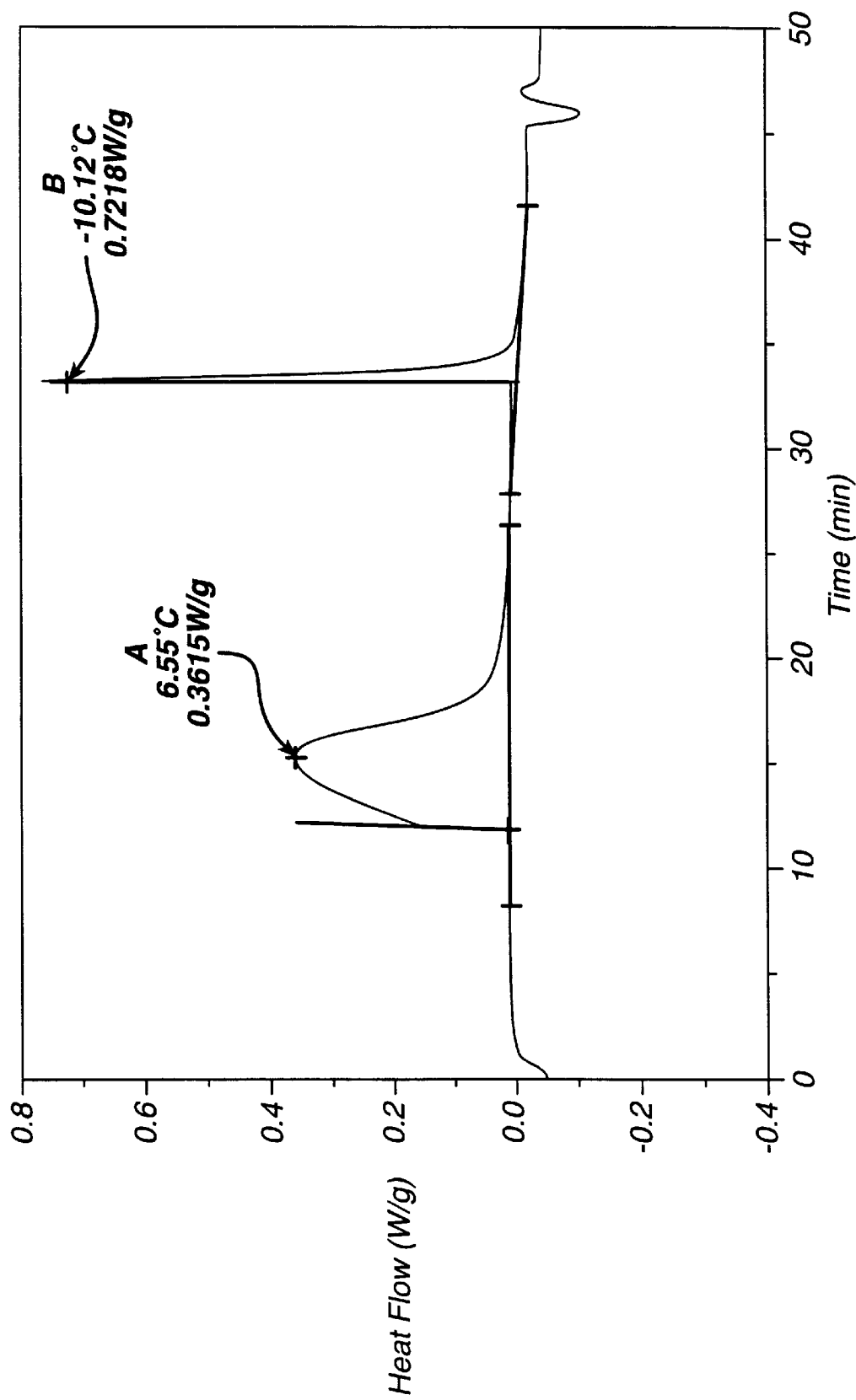
FIG. 5 is a DSC of a 10 percent weight by weight solution of a 35/65 mole percent ε-caprolactone-co-glycolide in 1,4-dioxane. The A and B on the DSC indicates the solidification of the mixture and the C is the apparent glass transition temperature of the mixture (on cooling). To observe these thermal events the cooling rates should be approximately 1 degree a minute.

After the polymer solvent mixture is formed the mixture is then solidified. For a specific polymer-solvent system, the solidification point, the melt temperature and the apparent glass transition of the polymer-solvent system can be determined using standard differential scanning calorimetric (DSC) techniques. In theory, but in no way limiting the scope of the present invention, it is believed that as a polymer solvent system is cooled down an initial solidification occurs at about or below the freezing point of the solvent. This corresponds to the freezing of a substantial portion of the solvent in the system. The initial freezing appears as a first exothermic peak. A second freezing point occurs when the remaining solvent associated with the polymer solidifies. The second freezing point is marked by a second exothermic peak. The apparent Tg is the temperature at which the fully frozen system displays the first endothermic shift on reheating. One example of an apparent Tg is illustrated in FIG. 5.

An important parameter to control is the rate of freezing of the polymer-solvent system. The type of pore morphology that gets locked in during the freezing step is a function of the solution thermodynamics, freezing rate, which may control whether it is spinodal or binodal, temperature to which it is cooled, concentration of the solution, homogeneous or heterogenous nucleation etc. Detailed description of these phase separation phenomenon can be found in the references provided herein ("Microcellular foams via phase separation" by A. T. Young, J. Vac. Sci. Technol. A 4(3), May/June 1986; and "Thermodynamics of Formation of Porous Poymeric Membrane from Solutions" by S. Matsuda, Polymer J. Vol. 23, No. 5, pp 435–444, 1991).

In the prior art the polymer-solution was frozen by a rapid quenching step. Quenching for aliphatic polyesters was commonly to low temperature such as either −40° C. or −176° C. using liquid nitrogen. Although, these techniques may be used we have also discovered that freezing aliphatic polyester solutions at a slow rate will also work. In the preferred embodiment this would mean cooling the shelf of the lyophilizer and the polymer solution in the mold from room temperature to approximately 5 degrees below the solidification point at a rate equal to or less than 1° C./min and less than preferably at 0.5° C./min. This slow cooling step unexpectedly overcame the problems associated with the non-uniform microstructure of the foams through the thickness in the prior art. This method provided foams with a random and uniform microstructure.

The polymer solution previously described can be solidified in a variety of manners such as placing or injecting the solution in a mold and cooling the mold in an appropriate bath or on a refrigerated shelf. Alternatively, the polymer solution can be atomized by an atomizer and sprayed onto a cold surface causing solidification of the spray layer by layer. The cold surface can be a medical device or part thereof or a film. The shape of the solidified spray will be similar to the shape of the surface it is sprayed onto. Alternatively, the mixture after solidification can be cut or formed to shape while frozen.

Additionally, another method to make shaped foamed parts is to use a cold finger (a metal part whose surface represents the inside of the part we want to fabricate). The cold finger is dipped into a mixture of polymer in an appropriate solvent and removed. This is much like dipping an ice cream pop into warm chocolate that freezes to a hard, cold skin, or dipping a form into a latex of rubber to form gloves or condoms. The thickness and morphology of the foam produced are a function of the temperature, dwell time and withdrawal rate of the cold finger in the mixture. Longer dwell, colder finger and slower withdrawal will produce a thicker coating. After withdrawal, the cold finger is placed on a fixture of large thermal mass that is in contact with the refrigerated tray of the lyophilized. From this point the primary and secondary drying processes are as described above.

Alternatively, the polymer solution can be solidified with various inserts incorporated with the solution such as films, scrims, woven, nonwoven, knited or braided textile structures. Additionally, the solution can be prepared in association with another structure such an orthopedic implant or vascular or branched tubular construct (as a scaffold for a vascularized or ducted organ).

The polymer solution in a mold undergoes directional cooling through the wall of the mold that is in contact with the freeze dryer shelf, which is subjected to a thermal cycle. The mold and its surface can be made from virtually any material that does not interfere with the polymer-solvent system, though it is preferred to have a highly conducting material. The heat transfer front moves upwards from the lyophilizer shelf through the mold wall into the polymer solution. The instant the temperature of the mixture goes below the freezing point the mixture also phase separates in one of the four ways described above.

The morphology of this phase separated system is locked in place during the freezing step of the lyophilization process and the creation of the open pores is initiated by the onset of vacuum drying resulting in the sublimation of the solvent. However, the mixture in container or mold that is cooled from a heat sink will solidify prior to completely freezing. Although the mixture may appear solid, initially there appears to be some residual solvent associated with the polymer that has not cystallized. It is theorized, but in no way limiting the present invention, that a freezing front moves through the mixture from the heat sink to complete the solidification after the mixture has apparently solidified. The material in front of the freezing front at a given time will not be as cold as the material behind the front and will not be in a completely frozen state.

We have discovered that if a vacuum is applied to the apparently solid polymer-solvent mixture immediately after it appears to solidify, a foam with a gradient structure having variable pore size and structure as well as channels can be created. Therefore, timing of the onset of the sublimation process (by pressure reduction i.e. vacuum drying) is a critical step in the process to create transitions in the structure. The timing of the onset of sublimation will be affected by the thickness of the foam being made, concentration of the solution, rate of heat transfer, and directionalities of the heat transfer. Those skilled in the art will appreciate that this process can be monitored and characterized for specific polymer-solvent systems by using thermocouples and monitoring the heat transfer rates of the foams at various depths and locations in the device being foamed. By controlling the sublimation process, structures with a gradient in pore morphology and anisotropy may be created. This process can lead to the creation of microstructures that mimic tissues such as cartilage, bone and skin. For example, channels will generally be formed if a vacuum is pulled immediately after the solution apparently solidifies. However, if the same solution is allowed to solidify further the foam will have larger pores closer to the surface where the vacuum is being drawn (opposite the heat sink) and smaller pores closer to the heat sink.

This process is the antitheses of the prior art process that focused on creating foams with a uniform microstructure (randomly interconnected pores), whereby the whole solution is completely frozen. And vacuum drying is applied only after a considerable amount of time is given for the completion of desired phase separation (U.S. Pat. No. 5,755,792 (Brekke); U.S. Pat. No. 5,133,755 (Brekke); U.S. Pat. No. 5,716,413 (Walter, et al); U.S. Pat. No. 5,607,474 (Athanasiou, et al); U.S. Pat. No. 5,686,091 (Leong, et al); U.S. Pat. No. 5,677,355 (Shalaby, et al); and European disclosures E0274898 (Hinsch) and EPA 594148 (Totakura)).

Figure 4:
FIG. 4 is a scanning electron micrograph of bottom surface of a foam formed by using the inventive foaming process. The bottom surface of the foam forms a substantially nonporous barrier that will inhibit the migration of cells.

Foams with various structures are shown in FIGS. 2, 3, and 4. As can be seen from in FIG. 2 the pores orientation, size, and shape. For example, as shown in FIG. 2 the orientation of the major axis of the pores may be changed from being in the same plane as the foam to being oriented perpendicular to the plane of the foam. By way of theory, but in no way limiting the scope of this invention, it is believed that this in conventional foam processing as the solvent crystallizes a freezing front moves through the solution solidifying the solution in crystalline layers parallel to the freezing front. However, if a vacuum is pulled before the solution completely freezes, the morphology of the foam results in pores being formed generally aligned parallel to the vacuum source. As is illustrated in FIG. 2.

Figure 2A:
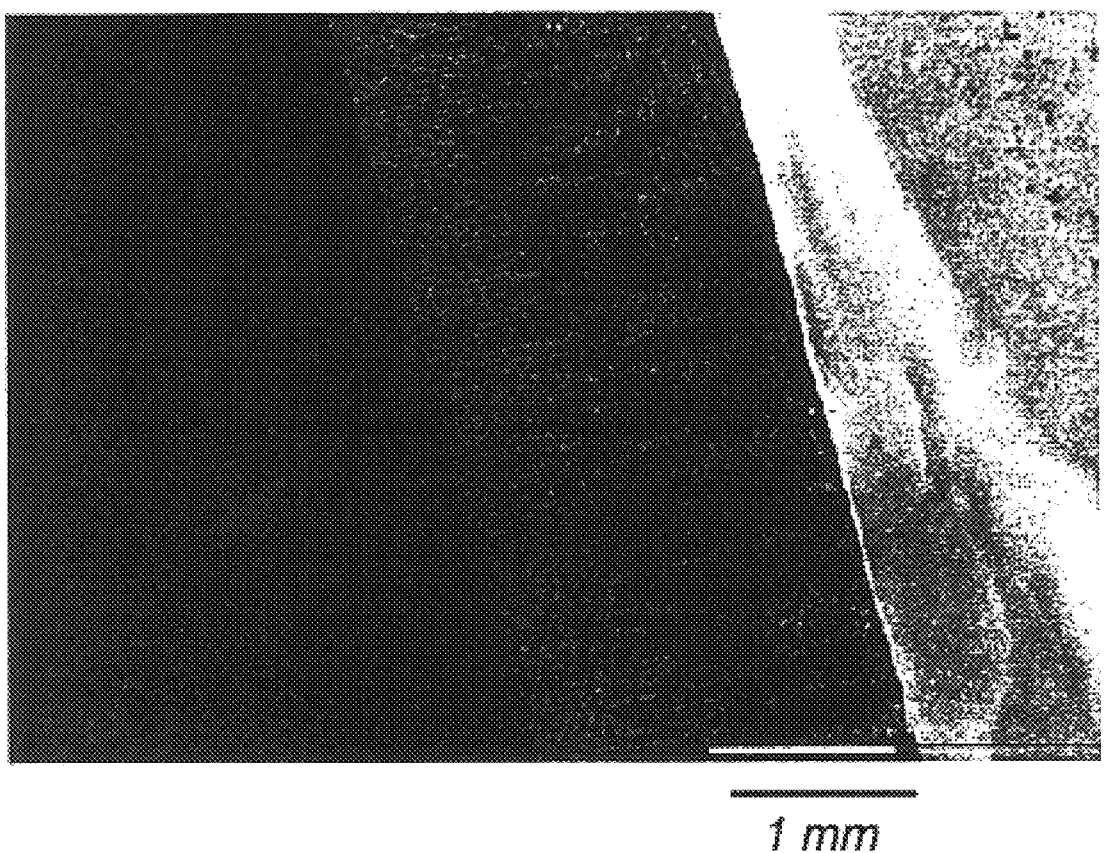
FIGS. 2A and 2B are scanning electron micrographs that illustrates the different architecture that can be made using the inventive foaming process.

As can be seen from FIG. 2A the pore size can be varied from a small pore size generally between about 10 microns and about 60 microns to a larger size of from about 60 microns to about 200 microns in a porous gradient foam. Again this results from pulling a vacuum on the apparently solidified solution before it is completely solidified. The polymer concentration in the solution and the cooling rates are also important parameters in controlling the cell size. Ideally the foam structure could be created to serve as a template to restore human tissue junctions such as the cartilage to bone junction present in joints. This foam would progress form a small round pores to larger column-like (i.e. with a diameter to length ratio of at least 2 to 1) pores. Additionally, the stiffness of the foam can controlled by the foams structure or blending two different polymers with different Young's moduli.

Figure 2B:
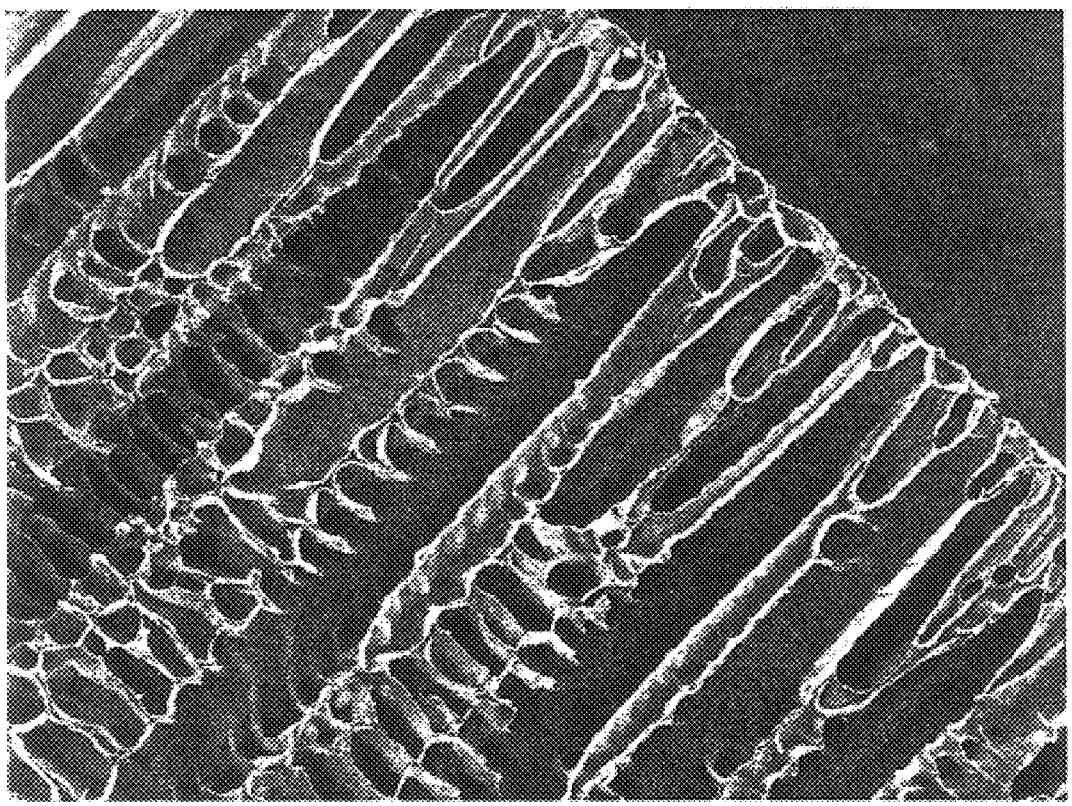
Figure 3A:
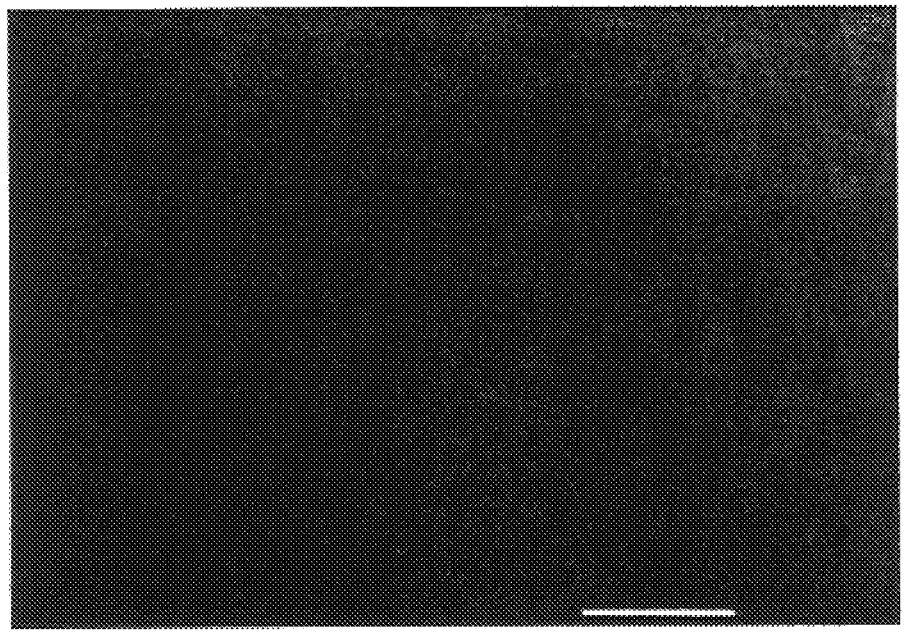
FIGS. 3A, 3B, 3C and 3D are scanning electron micrographs of micro-patterning on top surface of four foams formed by using the inventive foaming process.
Figure 3B:
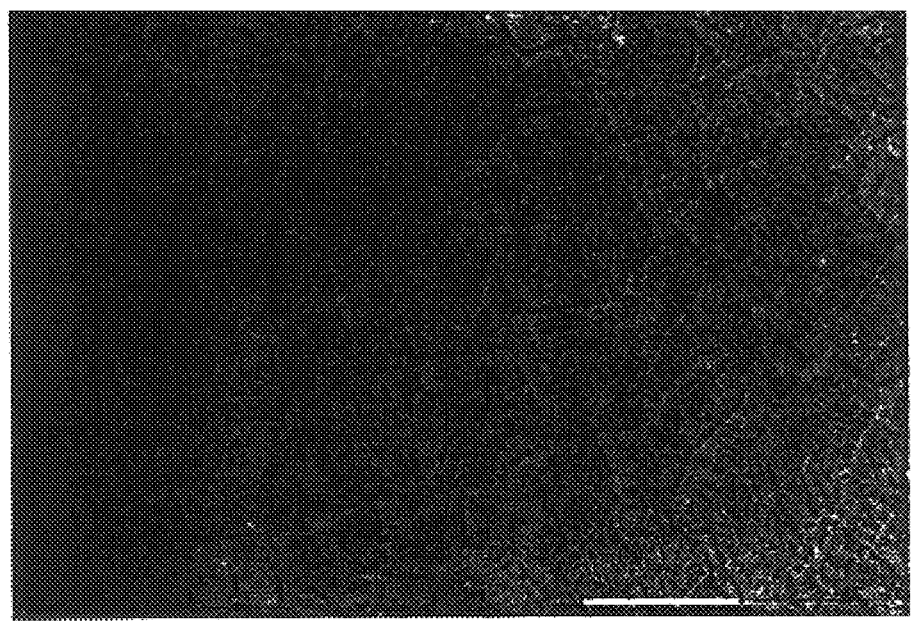
Figure 3C:
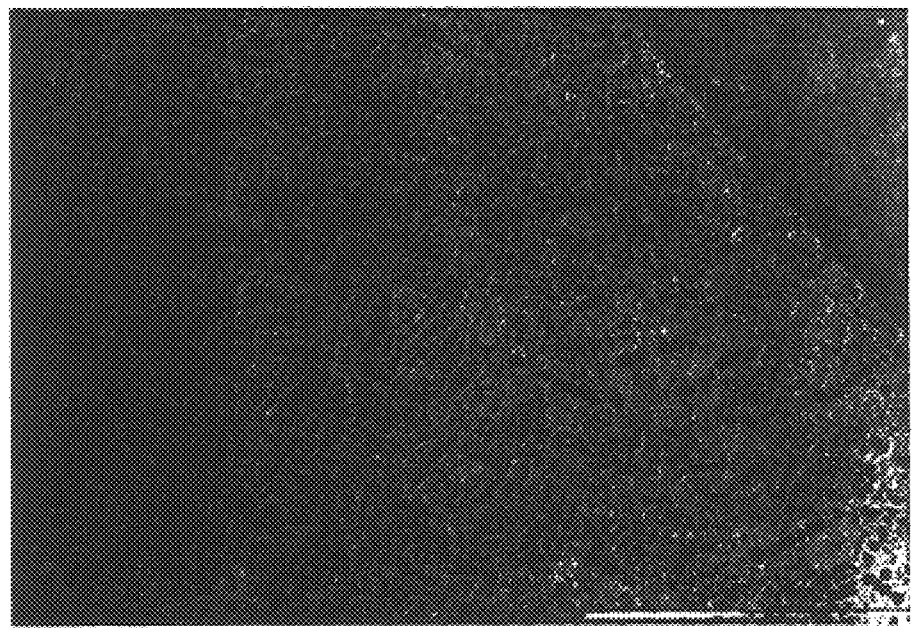
Figure 3D:
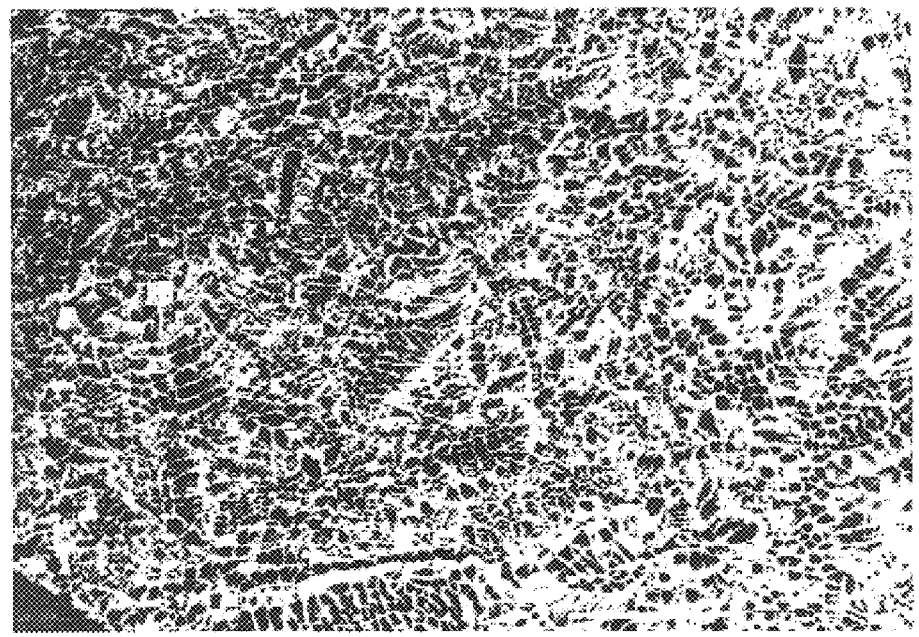

Foams can also have channels as is illustrated in FIG. 2B. The channels formed by this process may traverse the thickness of the foam and generally range in diameter from about 30 to about 200 microns in diameter. The channels generally are at least two times the channel's average diameter and preferably are at least four times the channel's average diameter and most preferably at least eight times the channel's average diameter. The channel size and diameter of course will be selected based on the desired functionality of the channel such as cell invasion, nutrient diffusion or as a avenue for vascularization. These structures are more fully described in copending patent application entitled Porous Tissue Scaffoldings for the Repair or Regeneration of Tissue, filed on Jun. 30, 1999, assigned to Ethicon, Inc, having a docket number of ETH-1347 (hereby incorporated by reference).

One skilled in the art can easily visualize that such a directionality can be created in any three dimensions by designing an appropriate mold and subjecting the walls of such a mold to different temperatures if needed. The following types of gradient structures can be made by variation in the pore size and/or shape through the thickness with a uniform composition: pores of one type and size for a certain thickness followed by another type and size of pores, etc; compositional gradient with predominantly one composition on one side and another one on the other with a transition from one entity to the other; a thick skin comprising low porosity of low pore size layer followed by a large pore size region; foams with vertical pores with a spatial organization these vertical pores can act as channels for nutrient diffusion the making of these in 3D molds to create 3D foams with the desired microstructure combinations of compositional and architectural gradient. Generally the foams formed in containers or molds will have a thickness in the range of from about 0.25 mm to about loomm and preferably will have a thickness of from about 0.5 mm to about 50 mm. Thicker foams can be made but the lyophilization cycle times may be quite long, the final foam structures may be more difficult to control and the residual solvent content may be higher.

As previously described the inventive process cycle for producing biocompatible foam is significantly reduced by performing the sublimation step above the apparent glass transition temperature and below the solidification temperature of the mixture (preferably just below the solidification temperature). The combined cycle time of (freezing+primary drying+secondary drying) is much faster than is described in the prior art. For example, the combined cycle for aliphatic polyesters using volatile solvents is generally less than 72 hours, preferably less than 48 hours, more preferably less than 24 hours and most preferably less than 10 hours. In fact the combined cycle can be performed with some aliphatic polyesters in less than 3 hrs for foams of thickness 1 mm or less; less than 6 hrs for foams of thickness around 2 mm and less than 9 hrs for foams of thickness around 3 mm. Compare this with prior art which is typically 72 hrs or greater. The residual solvent concentrations in these foams made by this process will be very low. As described for aliphatic polyesters foams made using 1,4-dioxane as a solvent the residual concentration of 1,4-dioxane was less than 10 ppm (parts per million) more preferably less than 1 ppm and most preferably less than 100 ppb (parts per billion).

In another embodiment of the present invention, the polymers and blends that are used to form the foam can be used as a drug delivery matrix. To form this matrix, the polymer would be mixed with a therapeutic agent prior to forming the foam or loaded into the foam after it is formed. The variety of different therapeutic agents that can be used in conjunction with the foams of the present invention is vast. In general, therapeutic agents which may be administered via the pharmaceutical compositions of the invention include, without limitation: antiinfectives such as antibiotics and antiviral agents; analgesics and analgesic combinations; anti-inflammatory agents; hormones such as steroids; growth factors (bone morphogenic proteins (i.e. BMP's 1–7), bone morphogenic-like proteins (i.e. GFD-5, GFD-7 and GFD-8), epidermal growth factor (EGF), fibroblast growth factor (i.e. FGF 1–9), platelet derived growth factor (PDGF), insulin like growth factor (IGF-I and IGF-II), transforming growth factors (i.e. TGF-β I–III), vascular endothelial growth factor (VEGF)); and other naturally derived or genetically engineered proteins, polysaccharides, glycoproteins, or lipoproteins. These growth factors are described in *The Cellular and Molecular Basis of Bone Formation and Repair* by Vicki Rosen and R. Scott Thies, published by R. G. Landes Company hereby incorporated herein by reference. Bioactive coatings or surface treatments could also be attached to the surface of the materials. For example, bioactive peptide sequences (RGD's) could be attached to facilitate protein adsorption and subsequent cell tissue attachment.

Matrix formulations may be formulated by mixing one or more therapeutic agents with the polymer used to make the foam or with the solvent or with the polymer-solvent mixture and foamed. Alternatively, the therapeutic agent could be coated on to the foam preferably with a pharmaceutically acceptable carrier. Any pharmaceutical carrier can be used that does not dissolve the foam. The therapeutic agent, may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001 percent to about 70 percent, more typically about 0.001 percent to about 50 percent, most typically about 0.001 percent to about 20 percent by weight of the matrix. The quantity and type of polymer incorporated into the drug delivery matrix will vary depending on the release profile desired and the amount of drug employed.

Upon contact with body fluids the drug will be released. If the drug is incorporated into the foam then as the foam undergoes gradual degradation (mainly through hydrolysis) the drug will be released. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like. Following this or similar procedures, those skilled in the art will be able to prepare a variety of formulations.

Additionally, radio-opaque markers may be added to the foam to allow imaging of the foam after implantation.

The following examples are illustrative of the principles and practice of this invention, although not limited thereto. Numerous additional embodiments within the scope and spirit of the invention will become apparent to those skilled in the art.

EXAMPLES

In the examples which follow, the polymers and monomers were characterized for chemical composition and purity (NMR, FT-IR), thermal analysis (DSC), molecular weight (inherent viscosity), and baseline and in vitro mechanical properties (Instron stress/strain).

$^1$H NMR was performed on a 300 MHz NMR using $CDCl_3$ or HFAD as a solvent. Thermal analysis of segmented polymers and monomers was performed on a Dupont 912 Differential Scanning Calorimeter (DSC). A Fisher-Johns melting point apparatus was also utilized to determine melting points of monomers. Inherent viscosities (I.V., dL/g) of the segmented polymers were measured using a 50 bore Cannon-Ubbelhode dilution viscometer immersed in a thermostatically controlled water bath at 25° C. utilizing chloroform or HFIP as the solvent at a concentration of 0.1 g/dL.

Example 1

Synthesis of a Random Poly(ε-caprolactone-co-glycolide)

A random copolymer of ε-caprolactone-glycolide with a 35/65 molar composition was synthesized by ring opening polymerization reaction. The method of synthesis was essentially the method described in U.S. Pat. No. 5,468,253 in Example 6 (which is hereby incorporated herein by reference). The amount of diethylene glycol initiator added was adjusted to 1.15 mmole/mole of monomer to obtain the following characteristics of the dried polymer: The inherent viscosity (I.V.) of the copolymer was 1.59 dL/g in hexafluoroisopropanol at 25° C. The molar ratio of PCL/PGA was found to be 35.5/64.5 by proton NMR with about 0.5% residual monomer. The glass transition (Tg) and the melting points (Tm) of the copolymer were found to be −1° C., 60° C. and 126° C. respectively, by DSC.

Example 2

Detemination of the Thermal Transition of a 10% (wt/wt) Solution of Poly(ε-caprolactone-co-glycolide) in 1,4-Dioxane A 10% wt./wt. (approximately) solution of the ε-caprolactone-co-glycolide described in Example 1 in 1,4-dioxane was prepared by dissolving 1 part by weight of the polymer to every 9 parts per weight of the solvent. The solution was prepared in a flask with a magnetic stir bar. For the copolymer to dissolve completely, it was gently heated to 60±5° C. and continuously stirred for a minimum of 4 hours but not exceeding 8 hours. Trace amounts of the polymer remained undissolved even after 8 hours of stirring. A clear homogeneous solution of the copolymer in 1,4-dioxane was then obtained by filtering the solution through an extra coarse porosity filter (Kimble, Kimax Buchner funnel with Kimflow fritted disc) using dry nitrogen to help in the filtration of this viscous solution.

Figure 6A:
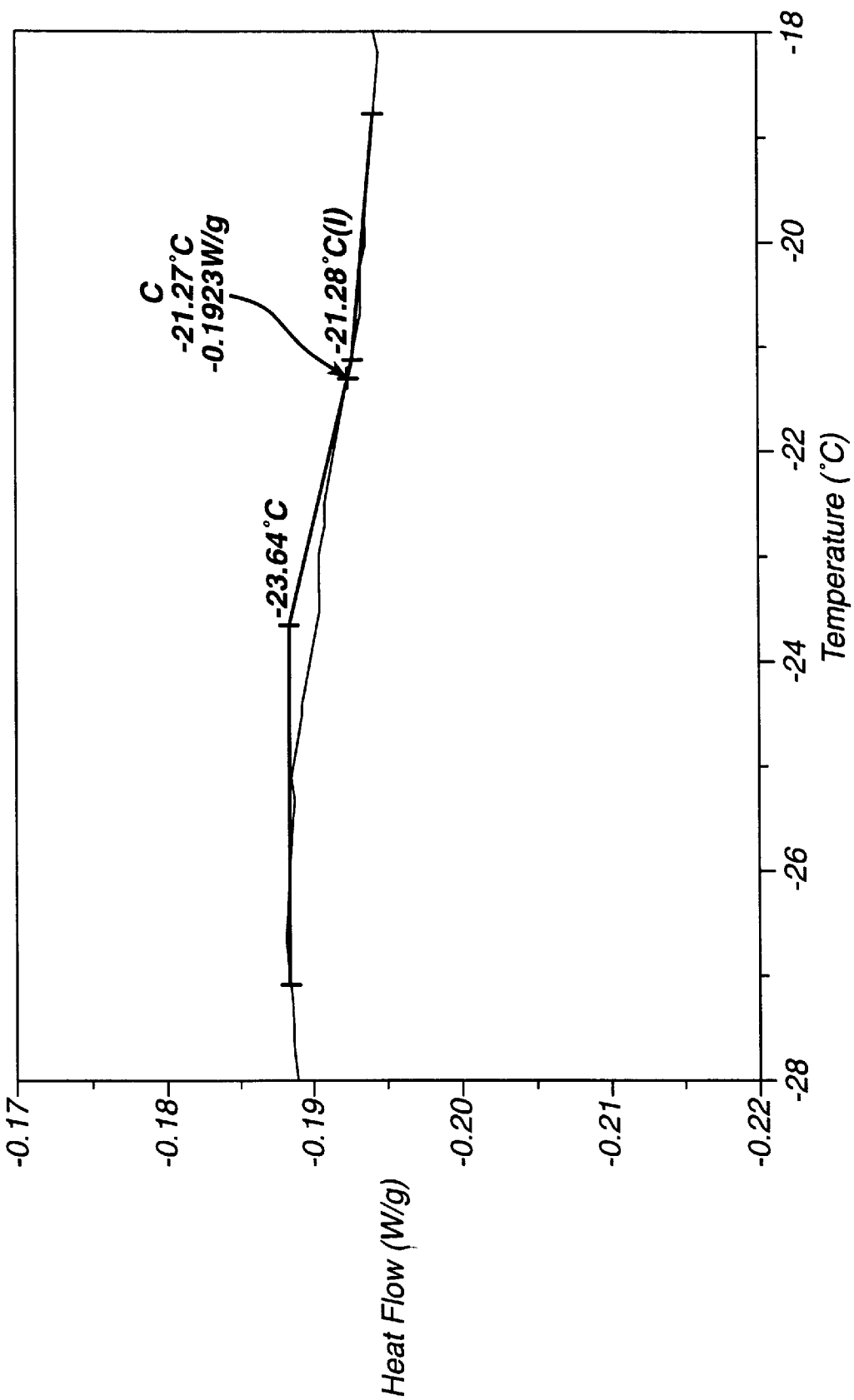

A differential scanning calorimetry (1° C./min) was used to determine the thermal transitions of the polymer solution described above. The freezing points for the polymer solution were about 6° C. and −10° C. and the melt downs were about 2° C. and about 13° C. The apparent glass transition of this system was around −21° C. (see FIGS. 5, 6A and 6B).

Example 3

Lyophilization Process of Poly(ε-caprolactone-co-glycolide)

A VIRTIS freeze dryer (Model Freezemobile 6) was powered up and the shelf chamber was maintained at 20° C. under dry nitrogen for approximately 30 minutes. Thermocouples to monitor the shelf temperature were hooked up for monitoring. The polymer solution (prepared as described in Example 2) was poured into a silanized glass dish just before the actual start of the cycle. The dish was a cylindrical trough made of optical glass and weighed 620 grams. The dish was 5.5 mm thick, the lip height was 2.5 cm, with a 21 cm outer diameter and a 19.5 cm inner diameter.

The glass dish with the solution was carefully placed (without tilting) on the shelf of the lyophilizer, which was maintained at 20° C. The cycle was started and the shelf temperature was held at 20° C. for 30 minutes for thermal conditioning.

The solution was then allowed to freeze to −5° C. by setting the shelf temperature also to −5° C., which results in a cooling rate of about 1° C./min.

After 1 hour of freezing, vacuum was applied to initiate primary drying of the 1,4-dioxane by sublimation. Two hours of primary drying under vacuum at −5° C. was needed to remove most of the solvent. At the end of this drying stage typically the vacuum level reached to about 50 mTorr or less.

Next, secondary drying under a 50 mTorr vacuum was done in two stages to remove the remaining 1,4-dioxane. First, the shelf temperature was raised to 5° C. and held for 1 hour and; second, it was raised to 20° C. and held for 1 hour.

At the end of the second stage, the lyophilizer was brought to room temperature and the vacuum was broken with nitrogen. The chamber was purged with dry nitrogen for approximately 30 minutes before opening the door. The foams were then removed from the dishes by simply lifting off the surface. These foams were then placed in labeled plastic bags and stored under nitrogen.

Example 4

Synthesis of 40:60 Poly(ε-caprolactone-co-L-lactide) by Sequential Addition

In the glove box, 100 μL (33 μmol) of a 0.33 M stannous octoate solution in toluene, 115 μL (1.2 mmol) of diethylene glycol, 24.6 grams (170 mmol) of L-lactide, and 45.7 grams (400 mmol) of ε-caprolactone were transferred into a silanized, flame dried, two neck, 250 mL round bottom flask equipped with a stainless steel mechanical stirrer and a nitrogen gas blanket. The reaction flask was placed in an oil bath already set at 190° C. and held there. Meanwhile, in the glove box, 62.0 grams (430 mmol) L-lactide were transferred into a flame dried, pressure equalizing addition funnel. The funnel was wrapped with heat tape and attached to the second neck of the reaction flask. After 6 hours at 190° C., the molten L-lactide was added to the reaction flask over 5 minutes. The reaction was continued overnight for a total reaction time of 24 hours at 190° C. The reaction was allowed to cool to room temperature overnight. The copolymer was isolated from the reaction flask by freezing in liquid nitrogen and breaking the glass. Any remaining glass fragments were removed from the copolymer using a bench grinder. The copolymer was again frozen with liquid nitrogen and broken off the mechanical stirring paddle. The copolymer was ground into a tared glass jar using a Wiley Mill and allowed to warm to room temperature in a vacuum oven overnight. 103.13 grams of 40:60 poly(ε-caprolactone-co-L-lactide) were added to a tared aluminum pan and then devolitilized under vacuum at 110° C. for 54 hours. 98.7 grams (95.7% by weight) of copolymer were recovered after devolitilization. The inherent viscosity was measured and found to be 1.1 dL/g $CHCl_3$ at 25° C. (c=0.1 g/dL). FTIR (cast film from $CHCl_3$ onto KBr window, $cm^{-1}$): 2993, 2944, 2868, 1759, 1456, 1383, 1362, 1184, 1132, 1094, 870, and 756. $^1$H NMR (400 MHz, HFAD/Benzene, ppm): δ 1.25, 2 broad lines (e); 1.35, 2 lines (f); 1.42, 3 lines; 1.55, 2 lines; 2.22, 3 lines ; 2.35, 4 broad lines; 4.01, 3 lines; 4.05, 3 lines; 4.2, quartet; 5.05, 3 broad lines; 5.15, 4 lines. Polymer composition by $^1$H NMR: 41.8% PCL, 57.5% PLA, 0.8% L-lactide, <0.1% ε-caprolactone. DSC (20° C./min, first heat): $T_m$=154.8° C., $\Delta H_m$=18.3 J/g. GPC (molecular weights determined in THF using poly(methyl methacrylate) standards, daltons): $M_w$=160,000, $M_n$=101,000, PDI=1.6.

Example 5

Determination of the Thermal Transition of a 10 Percent (wt/wt) Solution of a Copolymer of 40/60 Mole Percent ε-caprolactone-co-lactide in 1,4-Dioxane A 10% wt./wt. (approximately) solution of the ε-caprolactone-co-(L)lactide described in Example 4 in 1,4- dioxane was prepared by dissolving 1 part by weight of the polymer to every 9 parts per weight of the solvent. The solution was prepared in a flask with a magnetic stir bar. For the copolymer to dissolve completely, it was gently heated to 60±5° C. and continuously stirred for a minimum of 4 hours but not exceeding 8 hrs. A clear homogeneous solution of ε-caprolactone-co(L)lactide in 1,4-dioxane was then obtained by filtering the solution through an extra coarse porosity filter (Kimble, Kimax Buchner funnel with Kimflow fritted disc) using dry nitrogen to help in the filtration of this viscous solution.

A differential scanning calorimetry (at 1° C./min) was used to determine the thermal transitions of the polymer-solvent system. For the ε-caprolactone-co-lactide-Dioxane system with a 10% wt/wt loading, the freezing points are at 6 and −12° C. and the melt down temperature are around 2 and 12° C. The apparent glass transition of this system was around −22° C.

Example 6

Transcompositional Foam

This example describes the making of a foam that has a compositional gradient and not necessarily a morphological gradient. Such a foam is made from polymer solutions that have been made by physical mixtures of two or more polymers. This example describes a transcompositional foam made from 35/65 PCL/PGA and 40/60 PCL/PLA Step A. Preparing a solution mixture of 35/65 PCL/PGA and 40/60 PCL/PLA in 1,4 Dioxane In the preferred method the two separate solutions are first prepared (a) a 10% wt/wt polymer solution of 35/65 Cap/Gly and (b) a 10% wt/wt 40/60 PCL/PLA. Once these solutions are prepared as described in Example 1, equal parts of each solution was poured into a separate mixing flask. A homogeneous solution of this physical mixture was obtained by gently heating to 60±5° C. and continuously stirring using a magnetic stir bar for approximately 2 hours.

Step B. Lyophilization cycle

We used an FTS Dura Dry Freeze dryer with computer control and data monitoring system to make this foam. The first step in the preparation of such a foam was to generate a homogeneous solution as described in Step A. The solution was carefully filled into a dish just before the actual start of the cycle. The glass dish cylindrical trough that weighed 117 grams, with a 100 mm outer diameter and a 95 mm inner diameter. The lip height of the dish was 50 mm. The walls and the base of the dish were 2.5 mm thick. Next the following steps were followed in sequence to make a 25 mm thick foam with the transcompositional gradient:

(i). The solution filled dish was placed on the freeze dryer shelf and the solution conditioned at 20° C. for 30 minutes. The cycle was started and the shelf temperature was set to −5° C. with a freezing rate of 0.5° C./min.

(ii). The solution was held at the freezing condition (−5° C.) for 5 hours.

(iii). Vacuum was applied to initiate primary drying of the dioxane by sublimation and held at 100 milliTorr for 5 hours.

(iv). Next, secondary drying was done at 5° C. for 5 hours and at 20° C. for 10 hours. At each temperature the vacuum level was maintained at 20 mTorr.

(v). At the end of the second stage, the lyophilizer was brought to room temperature and the vacuum was broken with nitrogen. The chamber was purged with dry nitrogen for approximately 30 minutes before opening the door.

The foam has a gradient in chemical composition which is evident from a close scrutiny of the foam wall morphology as shown in FIGS. 4, 5 and 6. The gradient in the chemical composition was further supported by NMR data as detailed below:

Foam sample produced by the above method and which was approximately 25 mm thick was characterized for mole % composition. The foam sample is composed of a physical blend of PCL/PLA and PCL/PGA. Slices of the foam sample were prepared and analyzed to determine if the material is homogeneous. The sample slices were identified as 1) foam IA (top slice), 2) foam IB (top middle slice), 3) foam IC (bottom middle slice), 4) foam ID (bottom slice). The NMR sample preparation consisted of dissolving a 5 mg of material into 300 µL hexafluoroacetone sesqua deutrium oxide (HFAD) and then diluting with 300 µL of $C_6D_6$.

1H NMR Results: Mole % Composition

| Sample ID | PLA | PGA | PCL |
|---|---|---|---|
| Foam IA | 47.2 | 12.4 | 40.5 |
| Foam IB | 12.3 | 51.3 | 36.5 |
| Foam IC | 7.7 | 56.5 | 35.8 |
| Foam ID | 7.8 | 56.3 | 35.8 |

The NMR results indicate that the foam samples are heterogeneous with respect to composition. The top layer of the foam is high in PLA concentration (47 mole %), whereas the bottom layer of the foam is high in PGA concentration (56 mole %). These results suggest that the PCL/PGA copolymer and the PCL/PLA copolymer had differences in their phase separation behavior during the freezing step and formed a unique compositionally gradient foam.

Example 7

Preparation of a Foam with Vertical Channels

This example describes the making of a 35/65 Cap/Gly foam with vertical channels that would provide pathways for nutrient transport and guided tissue regeration.

We used a FTS Dura Dry Freeze dryer with computer control and data monitoring system to make this foam. First step in the preparation of such a foam was to generate a homogeneous solution. A homogeneous solution of 35/65 Cap/Gly was made as described in Example 2. The polymer solution was carefully filled into a dish just before the actual start of the cycle. The dish was a cylindrical trough made of optical glass and weighed 620 grams. The dish was 5.5 mm thick, the lip height was 2.5 cm, with a 21 cm outer diameter and a 19.5 cm inner diameter. Next the following steps are followed in sequence to make a 2 mm thick foam with the desired architecture:

(i). The solution filled dish was placed on the freeze dryer shelf that was precooled to −17° C. The cycle was started and the shelf temperature was held at −17° C. for 15 minutes to quench the polymer solution.

(ii). After 15 minutes of quenching to −17° C., a vacuum was applied to initiate primary drying of the dioxane by sublimation and held at 100 milliTorr for one hour.

(iii). Next, secondary drying was done at 5° C. for one hour and at 20° C. for one hour. At each temperature the vacuum level was maintained at 20 mTorr.

(iv). At the end of the second stage, the lyophilizer was brought to room temperature and the vacuum was broken with nitrogen. The chamber was purged with dry nitrogen for approximately 30 minutes before opening the door.

FIGS. 2A and 2B is a SEM pictures that shows a cross section of the foam with vertical channels. These channels can run through the thickness of the foam.

Example 8

Molded Foams

Two dimensional parts: Metal molds were made from aluminum and steel. The molds were coated to ensure release of the shaped part. The aluminum was coated with TUFRAN R-66™ and the steel was coated with a LECTROFLUOR 604™ release coating (General Magnaplate Corp. Linden, N.J.). The coatings were 0.002–0.003 inches and 0.001–0.002 inches thick respectively. The "wings" 3 on this part can be wrapped around a mandrel and bonded to make rings that can be used to hold the body of the part in a particular position relative to a medical device (such as a stapler cartridge or anvil). The mold was filled with polymer solution and lyophilized by the same technique that was used in Example 3.

Three dimensional parts: Molds can be made from porous metals that allow solvent vapors to pass through. The molds can be made from sintered brass or steel (for example Porcerax II™ from International Mold Steel, Inc.). The polymer solution can be poured into these mold, frozen and then evacuated as in the previous examples to make 3-D foams such as a cylinder. Additionally, these molds may contain inserts that the solutions may be poured around. The inserts can be a reinforcing materials, tubular structures (i.e. tubes for vascularizaion , ducts for secretion) or leachable salt structures. For example tubular structures could be provided to serve as an absorbable template for the growth of a vascular system. The inserts could be absorbable or nonabsorable biocompatible materials made by conventional processes such as molding, knitting, or weaving.

Another proposed embodiment of the present invention would be to use of a cold finger (a metal part whose surface represents the shape of the part we want to foam). The cold finger is dipped into the solvent polymer solution and removed. This is much like dipping an ice cream pop or cone into warm chocolate that freezes to a hard, cold skin. The thickness and morphology of the foam produced are a function of the temperature of the cold finger and the dwell time in the mixture. Longer dwell and colder finger will produce a thicker coating. After withdrawal from the mixture, the cold finger is placed on a fixture of large thermal mass that is in contact with the cold tray of the lyophilizer. From this point the primary and secondary drying processes are as described for the glass dish.

Mold variations: In addition to the 2-D, 3-D, and glass dish molds we have also made 2-D foams (thick and thin sheets) using square metal molds with 1" or 2" high walls and picture frame molds where the bottom surface is defined by the use of a plastic film that is not soluble in the solution solvent. The thin plastic film has the additional advantages of being disposable and thin enough to allow high rates of heat transfer.

A further embodiment of the present invention thermoformed plastic molds, with many cavities, can be used to lyophilize many individual small parts at one time. This mold could additionally be designed such that the individual cavities for the individual parts can be snapped apart or stamped out and the mold can be used as a packaging part for the foamed part. For example, foam part for a buttress material for linear cutter devices could for example be 60 mm×8 mm×1 mm in dimension such as is described in ETH1297 entitled "Foam Butress for Stapling Apparatus", filed on Jun. 30, 1999 assigned to Ethicon Inc (incorporated herein by reference). The cavity is molded into an additive free sheet of polypropylene. The parts are made, The individual mold cavities are punched out and then adhesive is applied to the foamed part. The cavity is covered with a protective film, paper is added. The polypropylene tray, foam paper and protective film are put in foil, sterilized and sealed. This package then becomes the dispenser package for application of the buttress to the linear cutter cartridge and anvil. The adhesive holds the buttress in position on the cutter device so that the buttress can be deployed at the stapleline site when fired. Absorbable adhesive can be used.

Example 9

Residual 1,4-Dioxane in Foams

A headspace GC method has found less than 0.1 ppm 1,4-dioxane in the inventive foams produced according to Example 3.

Details: An automated headspace sampler (Hewlett Packard 7694) was attached to a gas chromatograph (GC Hewlett Packard 5890 Series II). The conditions of both the autosampler and GC were set so that 1,4-dioxane could be eluted and detected.

Using this technique, a peak with the retention time of 1,4-dioxane was observed in two foam samples, and was estimated at 0.08 and 0.09 $\mu$g 1,4-dioxane/g foam, by comparison with a standard.

To a 21.3 mL vial is added 6 ul of water, with or without foam, with or without 1,4-dioxane. The water is to provide a constant headspace pressure. The capped vial is incubated 30 minutes at 115° C. and automatically injected. The separation is via an Alltech 6' by ⅛" 1% AT-1000 on Carbograph 1, 60/80 mesh column at 155° C. with the injector and FID at 170° C.

We claim:

1. A process for making biomedical absorbable foams comprising solidifying a solution of a solvent and a bioabsorbable polymer to form a solid, then with the solid at a temperature above the apparent Tg of the solid, but below the freezing temperature of the solid subliming the solvent out of the solid to provide a biocompatible porous foam.

2. The process of claim 1 wherein the bioabsorable polymer is an aliphatic polyester.

3. The process of claim 1 wherein the solvent is a liquid at room temperature.

4. The process of claim 2 wherein the aliphatic polyester is selected from the group consisting of homopolymers and copolymers of lactide, lactic acid, glycolide, glycolic acid), $\epsilon$-caprolactone, p-dioxanone (1,4-dioxan-2-one), trimethylene carbonate (1,3-dioxan-2-one), alkyl derivatives of trimethylene carbonate, δ-valerolactone, βbutyrolactone, γ-butyrolactone, $\epsilon$-decalactone, hydroxybutyrate, hydroxyvalerate, 1,4-dioxepan-2-one, 1,5,8,12-tetraoxacyclotetradecane-7,14-dione), 1,5-dioxepan-2-one, 6,6-dimethyl-1,4-dioxan-2-one and polymer blends thereof.

5. The process of claim 2 wherein the aliphatic polyester is an elastomer.

6. The process of claim 5 wherein the elastomer is selected from the group consisting of copolymers of $\epsilon$-caprolactone and glycolide; copolymers of $\epsilon$-caprolactone and lactide, copolymers of p-dioxanone (1,4-dioxan-2-one) and lactide, copolymers of $\epsilon$-caprolactone and p-dioxanone, copolymers of p-dioxanone and trimethylene carbonate, copolymers of trimethylene carbonate and glycolide, copolymer of trimethylene carbonate and lactide and blends thereof.

7. The process of claim 2 wherein additional present in the mixture is a second aliphatic polyester.

8. The process of claim 7 wherein the second aliphatic polyester is also soluble in the solvent.

9. The process of claim 1 wherein also present in the mixture are solids.

10. The process of claim 9 wherein the solids particles are selected from the group consisting of demineralized bone particles, calcium phosphate particles, calcium carbonate particles, nonsoluble aliphatic polyester particles and combinations thereof.

11. The process of claim 9 wherein also present is the mixture is a leachable solid.

12. The process of claim 1 wherein the leachable solid is selected from the group consisting of sodium chloride, potassium chloride, calcium chloride, sodium tartrate, sodium citrate, dextrose maltose, lactose and sucrose, alginate, gelatin and agarose.

13. The process of claim 1 wherein the mixture is placed into a mold.

14. The process of claim 13 wherein the mold also contains an insert.

15. The process of claim 1 wherein the solid is shaped prior to the solvent being sublimed from the solid.

16. The process of claim 1 wherein the mixture is solidified around a cold finger.

17. The process of claim 2 wherein the solvent is removed by subliming in less than 72 hours.

18. The process of claim 2 wherein the solvent is removed by subliming in less than 48 hours.

19. The process of claim 2 wherein the solvent is removed by subliming in less than 10 hours.

20. The process of claim 2 wherein also present in the mixture is a therapeutic agent.

21. The process of claim 20 wherein the therapeutic agent is selected from the group consisting of antiinfectives, hormones, analgesics, anti-inflammatory agents, growth factors and combinations thereof.

22. A process for making biomedical foams with channels therein comprising solidifying a mixture of a solvent and a bioabsorbable polymer to form a substantially solidified but not completely solidified material, then subliming the solvent out of the material to provide a biocompatible porous foam that has a porous structure with channels.

23. The process of claim 22 wherein the biomedical foams are processed to provide channels with an average diameter of from about 20 to about 200 microns.

24. The process of claim 23 wherein the channels are at least two times the average diameter in length.

25. The process of claim 23 wherein the channels are at least four times the average diameter in length.

26. The process of claim 22 wherein the porous foam structure is processed to have pores having a diameter that on average is from about 10 to about 200 microns.

27. The process of claim 22 wherein the bioabsorbable polymer is an aliphatic polyester.

28. The process of claim 22 wherein the solvent is a liquid at room temperature.

29. The process of claim 22 wherein the aliphatic polyester is selected from the group consisting of homopolymers and copolymers of lactide, lactic acid, glycolide, glycolic acid), $\epsilon$-caprolactone, p-dioxanone (1,4-dioxan-2-one), trimethylene carbonate (1,3-dioxan-2-one), alkyl derivatives of trimethylene carbonate, δ-valerolactone, βbutyrolactone, γ-butyrolactone, $\epsilon$-decalactone, hydroxybutyrate, hydroxyvalerate, 1,4-dioxepan-2-one, 1,5,8,12-tetraoxacyclotetradecane-7,14-dione), 1,5-dioxepan-2-one, 6,6-dimethyl-1,4-dioxan-2-one and polymer blends thereof.

30. The process of claim 22 wherein the aliphatic polyester is an elastomer.

31. A process for making biomedical foams with a gradient of pores therein comprising solidifying a mixture of a solvent and a bioabsorbable polymer to form a substantially solidified but not completely solidified material, then subliming the solvent out of the material to provide a biocompatible porous foam that has a gradient of pore sizes.

32. The process of claim 31 wherein the bioabsorbable polymer is an aliphatic polyester.

33. The process of claim 31 wherein the solvent is a liquid at room temperature.

34. The process of claim 31 wherein the aliphatic polyester is selected from the group consisting of homopolymers and copolymers of lactide, lactic acid, glycolide, glycolic acid), $\epsilon$-caprolactone, p-dioxanone (1,4-dioxan-2-one), trimethylene carbonate (1,3-dioxan-2-one), alkyl derivatives of trimethylene carbonate, δ-valerolactone, βbutyrolactone, γ-butyrolactone, $\epsilon$-decalactone, hydroxybutyrate, hydroxyvalerate, 1,4-dioxepan-2-one, 1,5,8,12-tetraoxacyclotetradecane-7,14-dione), 1,5-dioxepan-2-one, 6,6-dimethyl-1,4-dioxan-2-one and polymer blends thereof.

35. The process of claim 31 wherein the aliphatic polyester is an elastomer.

36. The process of claim 8 wherein a solution of the first and second aliphatic polyester are cooled at a rate slow enough to allow phase separation upon solidifiction of the first and second aliphatic polyester.

* * * * *